(12) United States Patent
Meredith et al.

(10) Patent No.: US 9,717,466 B2
(45) Date of Patent: *Aug. 1, 2017

(54) SYSTEM FOR CONVERGENCE OF ALARMS FROM MEDICAL EQUIPMENT

(71) Applicant: AT&T Mobility II LLC, Atlanta, GA (US)

(72) Inventors: Sheldon Kent Meredith, Marietta, GA (US); Francisco Martinez, Cumming, GA (US); George Goehring, Decatur, GA (US)

(73) Assignee: AT&T Mobility II LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/269,028

(22) Filed: Sep. 19, 2016

(65) Prior Publication Data

US 2017/0000427 A1 Jan. 5, 2017

Related U.S. Application Data

(63) Continuation of application No. 14/549,521, filed on Nov. 20, 2014, now Pat. No. 9,449,496.

(51) Int. Cl.
*G08B 21/00* (2006.01)
*A61B 5/00* (2006.01)
(Continued)

(52) U.S. Cl.
CPC .............. *A61B 5/746* (2013.01); *A61B 5/002* (2013.01); *A61B 5/0015* (2013.01); *A61B 5/747* (2013.01);
(Continued)

(58) Field of Classification Search
CPC ....... A61B 5/746; A61B 5/002; A61B 5/0015; A61B 5/747; H04W 4/02; H04W 4/12;
(Continued)

(56) References Cited

U.S. PATENT DOCUMENTS 3,972,320 A 8/1976 Kalman
5,534,851 A 7/1996 Russek
(Continued)

FOREIGN PATENT DOCUMENTS

EP 2464283 A1 6/2012
WO WO 9913766 A1 3/1999
(Continued)

OTHER PUBLICATIONS

Paksuniemi, M., et al. "Wireless sensor and data transmission needs and technologies for patient monitoring in the operating room and intensive care unit." Engineering in Medicine and Biology Society, 2005. IEEE-EMBS 2005. 27th Annual International Conference of the. IEEE, 2006.

(Continued)

*Primary Examiner* — Anh V La

(57) ABSTRACT

A device for processing alarms includes a processor and a computer-readable medium storing instructions which, when executed by the processor, cause the processor to perform various operations. The operations include receiving a first alarm from a first diagnostic device and determining a location associated with a first user. When the location associated with the first user is determined to be proximate to a device, the operations further include presenting a first verbal alert indicating that the first diagnostic device is presenting the first alarm. When the location associated with the first user is determined to be not proximate to the device, the operations further include sending a first notification message to a first mobile device of the first user indicating that the first diagnostic device is presenting the first alarm.

19 Claims, 4 Drawing Sheets

(51) Int. Cl.

| | | |
|---|---|---|
| *G08B 21/18* | (2006.01) | |
| *G06Q 50/24* | (2012.01) | |
| *G08B 21/22* | (2006.01) | |
| *G08B 5/22* | (2006.01) | |
| *A61G 12/00* | (2006.01) | |
| *G08B 7/06* | (2006.01) | |
| *G08B 29/18* | (2006.01) | |
| *H04W 4/02* | (2009.01) | |
| *H04W 4/12* | (2009.01) | |
| *H04W 88/04* | (2009.01) | |

(52) U.S. Cl.
CPC ............. *A61G 12/00* (2013.01); *G06Q 50/24* (2013.01); *G08B 5/222* (2013.01); *G08B 7/06* (2013.01); *G08B 21/18* (2013.01); *G08B 21/22* (2013.01); *G08B 29/18* (2013.01); *H04W 4/02* (2013.01); *H04W 4/12* (2013.01); *H04W 88/04* (2013.01)

(58) Field of Classification Search
CPC ....... H04W 88/04; A61G 12/00; G08B 21/22; G08B 5/222; G08B 7/06; G08B 21/18; G08B 29/18; G06Q 50/24
USPC ....... 340/286.07, 686.1, 686.6, 573.1, 573.4, 340/539.13, 539.1, 539.21, 539.23, 572.1
See application file for complete search history.

(56) References Cited

U.S. PATENT DOCUMENTS

| | | | |
|---|---|---|---|
| 5,822,544 | A | 10/1998 | Chaco et al. |
| 5,842,978 | A | 12/1998 | Levy |
| 6,364,834 | B1 | 4/2002 | Reuss et al. |
| 6,406,426 | B1 | 6/2002 | Reuss et al. |
| 7,390,299 | B2 | 6/2008 | Weiner et al. |
| 7,433,827 | B2 | 10/2008 | Rosenfeld et al. |
| 7,612,679 | B1 | 11/2009 | Fackler et al. |
| 7,666,151 | B2 | 2/2010 | Sullivan et al. |
| 7,840,277 | B2 | 11/2010 | Matos |
| 8,082,160 | B2 | 12/2011 | Collins et al. |
| 8,175,895 | B2 | 5/2012 | Rosenfeld et al. |
| 8,454,506 | B2 | 6/2013 | Rothman et al. |
| 8,510,126 | B2 | 8/2013 | Martin et al. |
| 8,803,700 | B1 | 8/2014 | Wilson |
| 9,449,496 | B2 * | 9/2016 | Meredith ............... A61G 12/00 |
| 2005/0242928 | A1 | 11/2005 | Kirkeby |
| 2007/0142716 | A1 | 6/2007 | Biondi |
| 2010/0115002 | A1 | 5/2010 | Antinoro et al. |
| 2010/0309002 | A1 | 12/2010 | Duvall |
| 2011/0270631 | A1 | 11/2011 | Cambray et al. |
| 2013/0027411 | A1 | 1/2013 | Hebler et al. |
| 2013/0300548 | A1 | 11/2013 | Robinson et al. |
| 2014/0240106 | A1 | 8/2014 | Kodama |
| 2014/0275856 | A1 | 9/2014 | Kohlrausch et al. |
| 2015/0070187 | A1 * | 3/2015 | Wiesner ............... A61B 5/0022 340/870.02 |

FOREIGN PATENT DOCUMENTS

| | | |
|---|---|---|
| WO | WO 2005050523 A2 | 6/2005 |
| WO | WO 2005114524 A2 | 12/2005 |
| WO | WO 2013150523 A1 | 10/2013 |
| WO | WO 2014014916 A2 | 1/2014 |

OTHER PUBLICATIONS

Padoy, Nicolas, et al. "On-line Recognition of Surgical Activity for Monitoring in the Operating Room." AAAI. 2008.

Schmid, Felix, et al. "The wolf is crying in the operating room: patient monitor and anesthesia workstation alarming patterns during cardiac surgery." Anesthesia & Analgesia 112.1 (2011): 78-83.

Shnayder, Victor, et al. "Sensor networks for medical car." SenSys. vol. 5. 2005.

Stankovic, J.A., et al. "Wireless sensor networks for in-home healthcare: Potential and challenges." High confidence medical device software and systems (HCMDSS) workshop. 2005.

Milenkovic, Aleksander, Chris Otto, and Emil Jovanov. "Wireless sensor networks for personal health monitoring: Issues and an Implementation." Computer communication 29.13 (2006): 2521-2533.

Jafari, Roozbeh, et al. "Wireless sensor networks for health monitoring." Mobile and Ubiquitous Systems: Networking and Services, 2005. MobiQuitous 2005. The Second Annual International Conference on. IEEE, 2005.

* cited by examiner

SYSTEM FOR CONVERGENCE OF ALARMS FROM MEDICAL EQUIPMENT

This application is a continuation of U.S. patent application Ser. No. 14/549,521, filed Nov. 20, 2014, now U.S. Pat. No. 9,449,496, which is herein incorporated by reference in its entirety.

Embodiments of the present disclosure relate to medical device alarms, and more specifically to systems for prioritizing alarms, generating verbal alerts, and/or sending notifications to remote medical personnel.

BACKGROUND

A typical operating room may include various diagnostic machines that may be monitoring a patient's blood pressure, blood sugar, carbon dioxide level, oxygen level, heart rate, and so forth. Each of these diagnostic machines may have one or more independent alarms that are typically expressed by an audible alert, e.g., a beeping sound. During an operation, it is often the case that one or more of these alarms will activate. The surgeon and other support staff may spend up to fifteen seconds or more trying to figure out which diagnostic device is generating the audible alarm. Occasionally, the time spent trying to determine the cause of the alarm is the difference between life and death in the operating room. In addition, in settings such as in an intensive care unit (ICU), doctors, nurses, and other medical staff regularly leave a patient's room and therefore may not hear the audible alarms. To address this situation, diagnostic machines may be wired to a front desk or nurse's station. However, if the nurse is away from the desk for any reason, such alarms may go unnoticed as well.

SUMMARY

The present disclosure describes devices, computer-readable media and methods for processing alarms. For example, in one embodiment a device includes a processor and a computer-readable medium. The computer-readable medium stores instructions which, when executed by the processor, cause the processor to perform various operations. The operations include receiving a first alarm from a first diagnostic device and determining a location associated with a first user. When the location associated with the first user is determined to be proximate to a device, the operations further include presenting a first verbal alert indicating that the first diagnostic device is presenting the first alarm. When the location associated with the first user is determined to be not proximate to the device, the operations further include sending a first notification message to a first mobile device of the first user indicating that the first diagnostic device is presenting the first alarm.

BRIEF DESCRIPTION OF THE DRAWINGS

The teaching of the present disclosure can be readily understood by considering the following detailed description in conjunction with the accompanying drawings, in which.

To facilitate understanding, identical reference numerals have been used, where possible, to designate identical elements that are common to the Figures.

DETAILED DESCRIPTION

Figure 1:
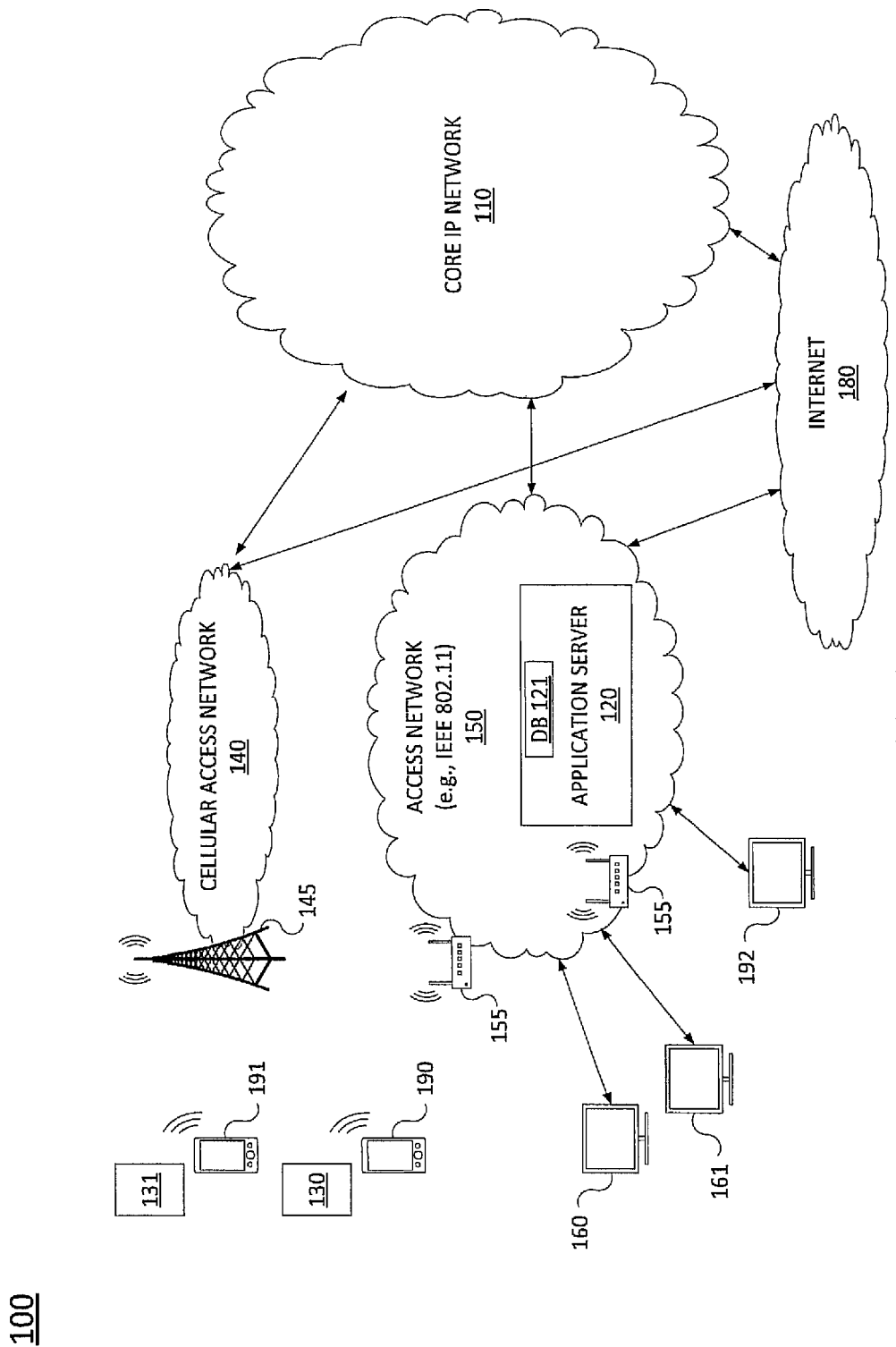
FIG. 1 illustrates an example network related to the present disclosure.

The present disclosure relates to a central device in a medical venue, such as in an operating room, in a patient's room in an intensive care unit (ICU), in a nursing home, or similar setting, that interfaces with different diagnostic devices over wireless connections, such as Bluetooth or Wireless Fidelity (Wi-Fi), or over wired connections, e.g., an Ethernet local area network (LAN), or the like. In one example, the central device presents an audible output that indicates which one of the diagnostic machines is generating an alarm, e.g., via machine-generated speech, as well as details of the cause of the alarm. For example, when a blood pressure monitor generates an audible alarm (e.g., a beeping sound) when it detects that a patient's blood pressure has fallen below a threshold value, e.g., less than 90/60 mmHg, such audible alarm may be suppressed at the blood pressure monitor, while the central device may generate an audible output such as "warning, blood pressure has fallen below ninety over sixty" or "warning, blood pressure is currently eighty over fifty." In one example, the central device may also have an integrated or attached display to show which diagnostic device is generating the alarm, as well as the details of such alarm.

In addition, the central device may send notifications messages relating to such alarms by short message service (SMS), multimedia message service (MMS) messages, or via email to mobile devices of medical personnel (broadly, medical "staff members") who are remote from the central device and the diagnostic devices. In particular, the central device may include a toggle switch that allows staff members to indicate when they are present in the room and to indicate when they depart from the room. Alternatively, or in addition, each staff member may be assigned a radio frequency identification (RFID) tag. Accordingly, the central device may be equipped with an RFID reader that is integral to the central device, or that is placed at the entrance to the room and connected to the central device for determining a presence of a staff member when his or her RFID tag is detected. As an alternative, instead of an RFID tag, the presence or proximity of a particular staff member may be detected by the central device via wireless detection of a mobile device of the staff member, e.g., detecting a media access control (MAC) address of the mobile device in wireless signals via a wireless transceiver of the central device.

In one example, the RFID signal strength, or wireless signal strength from a mobile device, is used as a proxy for distance, where if the signal strength is sufficiently high, it is determined that the staff member will likely hear the audible output from the central device that is located in the room. For example, the central device may store a predefined threshold signal strength value which, if exceeded, indicates that the user is proximate to the central device. Otherwise, the central device may assume that the staff member is not proximate to the central device and will not hear the audible output.

In another example, the central device may detect the presence of a staff member via a near-field communication (NFC) protocol, i.e., deliberate placement of an identification unit of the staff member within a few inches of the central device, or a reader of the central device, to indicate the presence of a particular staff member. The identification unit may comprise an RFID tag, a mobile device, e.g., a smart phone, an infrared communication device, or any other component equipped for NFC.

In one example, the central device may store a rule set for determining the manner in which the notifications of the detected alarms will be sent. In one example, the rule set comprises a list of all staff members to be notified, where remote notifications are suppressed for staff members with a presence indicated within the monitored room; otherwise, the pertinent mobile device(s) of the staff members who are deemed to be remote from monitored room will be notified by the central device via remote notifications. However, in some cases, not all notifications to the mobile devices need be suppressed, even if the staff member is present in the room. Likewise, in some cases a staff member may override remote notifications to all staff members, or to one or more other staff members, by activating a local switch or simply by being present in the room. For example, depending upon the patient, his or her specific conditions, and the determination of the medical provider, it may be deemed unnecessary to notify other staff members responsible for the patient's care who are not present in the room, so long as at least one responsible staff member is detected to be present in the monitored room.

In another example, the rules in the rule set may further involve consulting a schedule of staff members, which can be stored locally by the central device, or which can be stored by another machine within a same or a different network as the central device. For instance, the central device may determine who is "on-call" and who is not, such that only "on-call" staff members are notified of the diagnostic device alarms. The schedule of staff members and/or the rule set may further comprise information on modes of contacting the staff members, e.g., email addresses, mobile phone numbers for SMS messages, screen names/user names, e.g., for instant messaging, and so forth. In still another example, different rules may be applicable to different types of alarms from different diagnostic devices, even with respect to the same patient. It should be noted that the foregoing are just several examples of possible rule configurations in such a rule set. However, various rules can be devised by medical personnel based upon their professional judgment. In addition, the rules in the rule set can further be configured for all users, for groups of users, or on a user-by-user basis.

In one example, a notification may be sent via a local network of the medical venue, e.g., entirely within a hospital's own enterprise network. However, in another example, a notification may be sent via one or more of a cellular network, a core network, or the Internet in general. As mentioned above, a notification can take the form of a SMS or MMS message, an email, or similar communication. In addition, in one example, the notification may cause a mobile device to present an audio output, e.g., in the form of a machine-generated speech. For instance, the mobile device may generate an audio output that is the same or similar to a local audio output generated by the central device. For example, if the notification was triggered by an alarm from a blood pressure monitor that has detected that a patient's blood pressure has fallen below a threshold value, e.g., less than 90/60 mmHg, then the mobile device receiving a notification with such details may generate an audible output such as "warning, blood pressure has fallen below ninety over sixty." In this regard, the mobile device may be configured with an application that is tasked with receiving notifications of alarm conditions and generating local outputs on the mobile device, e.g., visual and/or audible outputs in response to the receipt of such notifications.

In one example, the present disclosure also provides for receiving a confirmation response from a mobile device that is notified. In particular, if a notification of an alarm is sent by the central device to one or more mobile devices of remote staff members, the central device may solicit acknowledgement responses from each of the staff members. For instance, a first staff member may respond first and indicate that he or she will address the alarm condition. As such, the central device may send an update message to the other mobile devices indicating that a particular staff member is currently addressing the alarm condition, thereby allowing the other staff members to attend to other patients and to other issues. In another example, the central device may escalate the notification beyond an initial group of staff members to be notified, e.g., if no acknowledgement is received within a threshold period of time. For example, an operator may set a threshold period of time of 15 seconds, 30 seconds, or any other duration of time, depending upon the particular alarm type, the particular conditions of the patient, and so forth.

In still another example, the central device of the present disclosure may rank or prioritize various alarms that may be provided to the medical staff, whether in the room or away from the room. For instance, if multiple diagnostic devices in the same room are generating alarms at the same time, the central device may determine, using a rule set that prioritizes different alarms in different circumstances, which alarms should be presented as verbal alerts and/or sent as notification messages first, and which should be presented later.

For instance, if a blood pressure monitor has detected that a patient's blood pressure has fallen below either or both threshold values of 90 mmHg systolic and 60 mmHg diastolic, this may trigger an alarm which is sent to the central device. However, these are not particularly low blood pressure values. For instance, 70/45 mmHg would be of greater concern, but may still not be life-threatening. On the other hand, a different diagnostic device, e.g., a breathing monitor, may detect that the patient is not breathing properly and issue an alarm to the central device. Thus, in the case of receiving simultaneous alarms for a blood pressure below 90/60 mmHg and a potential breathing issue, the central device may select to present the more critical alarm first. In other words, the central device may first generate a verbal alert as an audio output such as "warning, patient is not breathing properly" followed by a second verbal alert such as "warning, blood pressure is below ninety over sixty". Broadly, a verbal alert comprises a speech alert that is expressed in one or more words or one or more sentences. The speech alert can be a recording of a human uttering a particular set of words or sentences, or the speech alert can be computer or device generated speech (e.g., synthetic speech).

Similarly, a first notification message relating to the breathing issue may be sent to any remote mobile devices that are predefined to receive such a notification, followed by a second notification message relating to the blood pressure reading. In one example, the central device may wait until the first alarm condition is cleared, e.g., by medical personnel manually indicating that the first alarm condition is acknowledged and/or has been addressed, or simply by the completion of sending the first notification message and/or the completion of a first verbal alert relating to the first alarm.

The foregoing examples describe devices and techniques for processing alarms from one or more diagnostic devices, which are intended to reduce complications associated with high-risk medical environments such as operating rooms or intensive care rooms. Examples of the present disclosure allows medical personnel who are local to a central device to hear verbal alerts that draw their attention immediately to the particular diagnostic devices generating the alarms, rather than having to waste precious time trying to figure out the source of a beeping alarm. Examples of the disclosure also provide notifications of the alarm conditions to medical personnel who are not immediately in the presence of the central device. Furthermore, examples of the present disclosure can prioritize alarms from multiple diagnostic devices in the event of multiple simultaneous alarms, thereby helping to prevent staff members from wasting valuable time being distracted by non-critical or less critical alarms.

To aid in understanding the present disclosure, FIG. 1 illustrates in greater detail an example system 100 that is suitable for use in connection with processing alarms from one or more diagnostic devices, according to the present disclosure. Although the present disclosure is discussed below in the context of a particular system or network architecture, the present disclosure is not so limited. Namely, the present disclosure can be applied to any type of communication network that is capable of transmitting data, such as a local area network (LAN), a wireless local area network (WLAN), an Internet Protocol (IP) network, such as an Internet Protocol/Multi-Protocol Label Switching (IP/MPLS) core network, an IP Multimedia Subsystem (IMS) network, communications over the Internet in general, and so forth.

As shown in FIG. 1, the system 100 connects mobile devices 190, and 191, a workstation 192, and various diagnostic devices 160, and 161 with application server 120 via a core Internet Protocol (IP) network 110, a cellular access network 140, an access network 150 and/or Internet 180. In one embodiment, cellular access network 140 may comprise a radio access network implementing such technologies as: global system for mobile communication (GSM), e.g., a base station subsystem (BSS), or IS-95, a universal mobile telecommunications system (UMTS) network employing wideband code division multiple access (WCDMA), or a CDMA3000 network, among others. In other words, cellular access network 140 may comprise an access network in accordance with any "second generation" (2G), "third generation" (3G), "fourth generation" (4G), Long Term Evolution (LTE) or any other yet to be developed future wireless/cellular network technology. While the present disclosure is not limited to any particular type of cellular access network, in the illustrative embodiment, cellular access network 140 is shown as a UMTS terrestrial radio access network (UTRAN) subsystem. Thus, element 145 may comprise a Node B or evolved Node B (eNodeB).

In one embodiment, access network 150 may comprise a non-cellular access network such as a wireless local area network (WLAN), an IEEE 802.11 network, a "wired" access network, e.g., a local area network (LAN), an enterprise network, a metropolitan area network (MAN), a digital subscriber line (DSL) network, a cable network, a hybrid network utilizing a plurality of such technologies, and so forth. Thus, in one example access network 150 may include at least one wireless communication point 155, which may comprise a wireless access point/wireless router, an IEEE 802.11 access point, a ZigBee access point, a Bluetooth Low Energy (BLE) beacon, and so forth. In one example, access network 150 may include multiple wireless communication points 155 of different types. In one example, access network 150 may comprise a local network of a residence or business, e.g., a hospital, an enterprise network or the like. Thus, as illustrated in FIG. 1, mobile devices 190, and 191, workstation 192, and diagnostic devices 160, and 161 may have one or more wired or wireless connections to access network 150.

In one embodiment, mobile devices 190, and 191 may comprise any endpoint devices configured for wireless communication such as a personal computer, a laptop computer, a Wi-Fi device, a Personal Digital Assistant (PDA), a mobile phone, a smart phone, an email device, a computing tablet, a messaging device, and the like. In one embodiment, either or both of the mobile devices 190, and 191 may have both cellular and non-cellular access capabilities and may further have wired communication/networking capabilities. Notably, each of mobile devices 190, and 191 may also run a remote alert application which enables interactions with an application server (AS) (e.g., AS 120) for receiving notifications of diagnostic device alarms, for sending confirmation messages, and for presenting visual alerts or audible verbal alerts via a display screen and/or audio output unit, e.g., a speaker. In particular, mobile devices 190, and 191 may comprise devices associated with doctors, nurses or other medical staff that are carried by a person for receiving remote notifications of alarms from diagnostic devices. On the other hand, workstation 192 may comprise a substantially fixed-location desktop computer or similar device, e.g., deployed at a nurse's station, for similarly receiving and responding to notifications of diagnostic device alarms. In one example, each of the staff members associated with mobile devices 190, and 191 may also be assigned an identification tag 130, and 131, e.g., RFID tags which allow a central device within a room, such as AS 120, to detect the presence of a particular person within or sufficiently close to the room.

In one embodiment, core IP network 110 comprises a telecommunication service provider network with network devices or elements (not shown) which are capable of routing and forwarding IP packets between different hosts over the network. However, in one embodiment, the components of core IP network 110 may have additional functions, e.g., for functioning as a public land mobile network (PLMN)-General Packet Radio Service (GPRS) core network, for providing Voice over Internet Protocol (VoIP), Service over Internet Protocol (SoIP), and so forth, and/or may utilize various different technologies, e.g., Asynchronous Transfer Mode (ATM), Frame Relay, multi-protocol label switching (MPLS), and so forth. Thus, it should be noted that although core IP network 110 is described as an Internet Protocol network, this does not imply that the functions are limited to IP functions, or that the functions are limited to any particular network layer.

As illustrated in FIG. 1, access network 150 includes application server, e.g., AS 120, for processing alarms from one or more diagnostic devices. The application server 120 may also include a database (DB) 121 for storing instructions, e.g., rule set, and other information relating to processing alarms, in accordance with the present disclosure. For example, access network 150 may comprise a local network of a hospital, a nursing home or similar medical setting. Thus, in one embodiment, AS 120 may comprise any hardware server or computer that is well known in the art, and the database 121 may be any type of electronic collection of data that is also well known in the art. In one example, AS 120 may take the form of device 400 illustrated in FIG. 4 and described in greater detail below. The functions of AS 120 are also described in greater detail below in connection with FIG. 2, and with server 210 in particular.

The above network 100 is described to provide an illustrative environment in which embodiments of the present disclosure may be employed. In other words, the network 100 is merely illustrative of one network configuration that is suitable for implementing embodiments of the present disclosure. Thus, the present disclosure may also include any other different network configurations that are suitable for implementing embodiments of the present disclosure, for conveying communications among endpoint devices, for conveying communications between endpoint devices and other components (e.g., core network and access network components), and so forth. In particular, embodiments of the present disclosure may be implemented in any wired or wireless communication environment and may implement any communication technologies and protocols that enable devices to communicate, including: a cellular network, a wired and/or wireless local area network, a wide-area network, a wireless short-range peer-to-peer or mesh network, a satellite-based communication network, and Internet service provider access network, a layer 3 transport network, a combination of one or more of the foregoing network types, and so forth. Thus, those skilled in the art will realize that the communication system 100 may be expanded by including additional endpoint devices, access networks, network elements, application servers, etc., or modifying or substituting those illustrated in FIG. 1, without altering the scope of the present disclosure.

Figure 2:
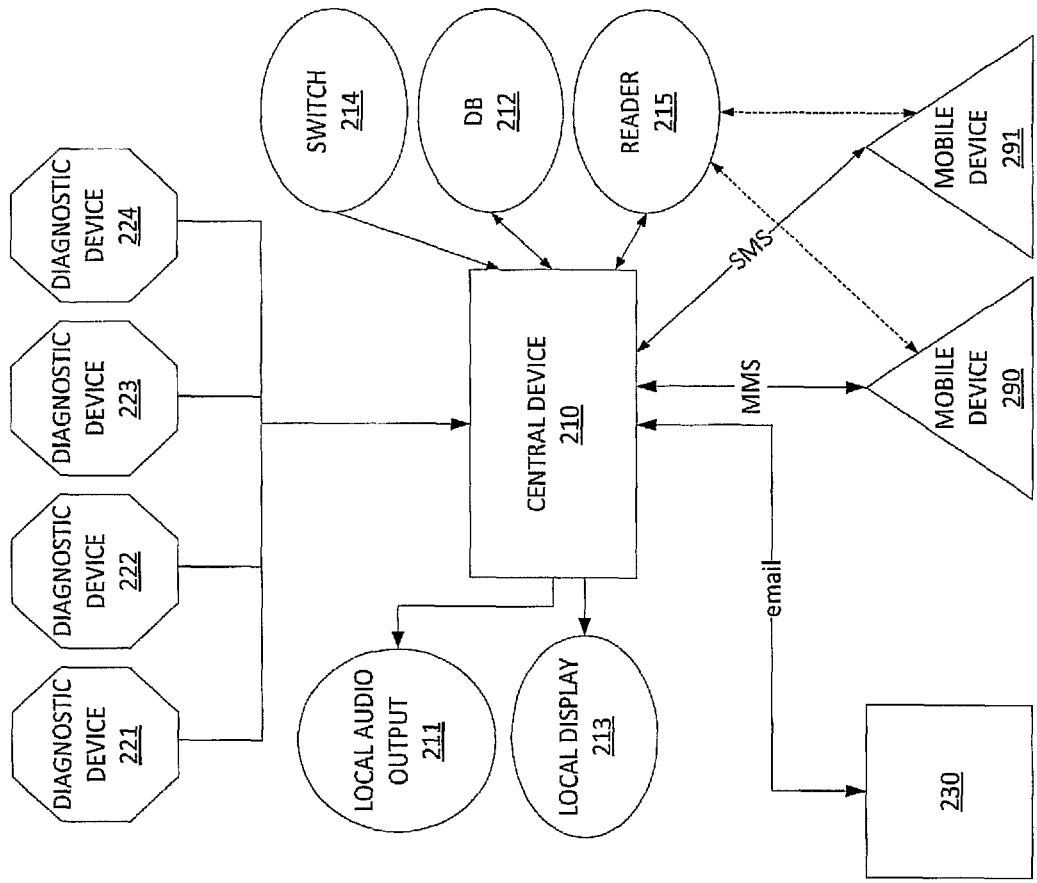
FIG. 2 illustrates an system with a central device, according to one embodiment of the present disclosure.

To further aid in understanding the present disclosure, FIG. 2 illustrates an example system 200 of the present disclosure for processing alarms from one or more diagnostic devices. System 200 includes a central device, or server 210 that is connected to and in communication with a number of diagnostic devices 221, 222, 223, and 224 via wired and/or wireless communication links. In one example, server 210 may be located within a same room as the diagnostic devices 221-224. In one example, the server 210 receives alarms from the diagnostic devices 221-224. Although, four diagnostic devices 221-224 are shown, it should be noted that any number of diagnostic machines may be deployed within a particular environment and be connected to and managed by the server 210. In addition, although it is contemplated that server 210 will be dedicated to a single room and a single patient, in another example, server 210 may coordinate and prioritize alarms from diagnostic devices for multiple patients in a single room, and send notification messages to remote staff members accordingly.

Server 210 may also be connected to or include an audio output unit 211, e.g., a speaker, for outputting machine-generated speech, and may include or be connected to another device storing a database (DB) 212. In one example, database 212 stores one or more rule sets for assisting in determining which remote devices should receive the notifications of alarms and under what circumstances, and for determining when and how to prioritize simultaneous alarms. In one example, server 210 may also be connected to or include a local display 213 for additionally generating visual outputs relating to alarms received from the diagnostic devices 221-224. Server 210 may further include or be connected to a switch 214 and/or a reader 215, e.g., an RFID reader, or a wireless transceiver, such as a Wi-Fi transceiver, a Bluetooth transceiver, a Bluetooth low energy (BLE) beacon or other near-field communication (NFC) device, and the like. In particular, reader 215 may detect the presence of staff members' RFID tags or mobile devices (e.g., mobile devices 290, or 291) for determining whether or not particular staff members should receive remote notifications. Thus, as an example, reader 215 is illustrated in FIG. 2 as communicating with mobile devices 290 and 291. Similarly, switch 214 may be used by staff members entering and leaving the room to manually indicate a presence near the server 210. It should be noted that some examples may include both a switch 214 and a reader 215, whereas other examples may only include one or the other of a switch 214 and a reader 215.

Also shown in system 200 are a workstation 230, and mobile devices 290, and 291, which may correspond to workstation 192 and mobile devices 190, and 191, respectively in FIG. 1. Although FIG. 2 illustrates the modes of communication between server 210 and workstation 230, mobile device 290 and mobile device 291 as being email, MMS and SMS, respectively, it should be noted that any one or more of these devices may be capable of communicating with central device 210 via multiple communication modalities, including these and others. Thus, in some cases, the communications between server 210 and workstation 230, mobile device 290 and mobile device 291 may occur entirely within a local network of server 210, or may traverse one or more service provider networks/public networks. For instance, mobile device 291 may be in a location remote from server 210 and may only be reachable via a cellular service provider network.

Figure 3:
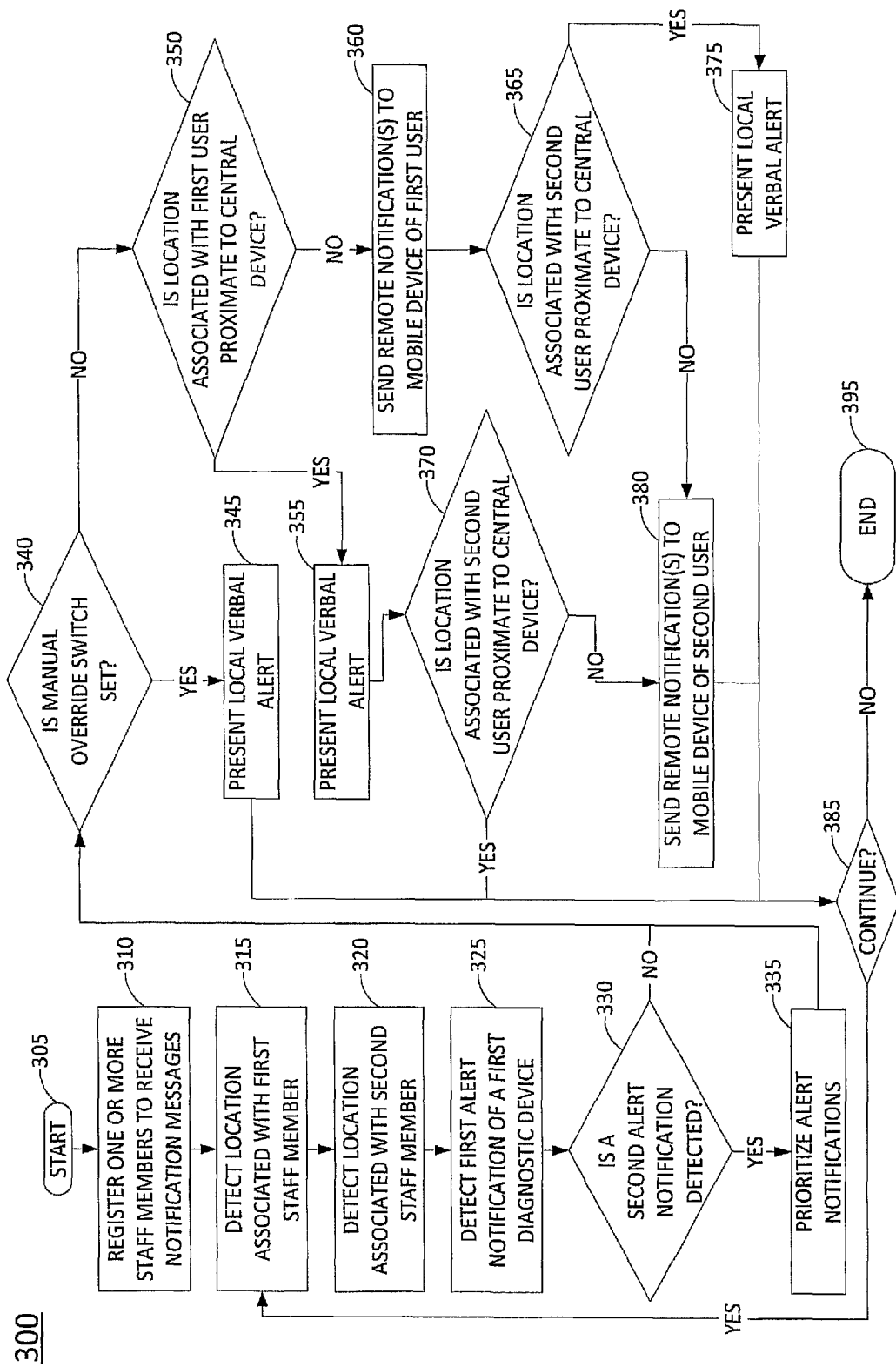
FIG. 3 illustrates a method of the present disclosure for processing diagnostic device alarms, according to one embodiment of the present disclosure.

FIG. 3 illustrates a flowchart of a method 300 of the present disclosure for processing diagnostic device alarms. In one embodiment, the method 300 is performed by a central device or server, such as AS 120 in FIG. 1 or server 210 in FIG. 2. Alternatively, or in addition, the steps, functions, or operations of method 300 may be performed by a device or system 400, and/or processor 402 as described in connection with FIG. 4 below.

Method 300 starts in step 305 and proceeds to step 310. In step 310, method 300 registers one or more users, e.g., staff members of a hospital, nursing home or other medical provider, to receive notification messages regarding alarms from one or more diagnostic devices that are managed by a central device. For example, a central device may be located within a same room as the one or more diagnostic devices and may include a user interface to allow one or more staff members to register to receiving notification messages from the central device. In one example, a single staff member may register himself or herself, as well as other staff members. In one example, the present disclosure may include an application installed on the mobile devices of staff members that interfaces to the central device to facilitate staff member registrations.

In one example, step 310 also includes retrieving schedule/calendar information for one or more staff members, e.g., from a storage device, determining which staff members are "on-duty" and which are not, and automatically registering one or more of the staff members who are "on-duty." In one example, the schedules of only staff members of a particular group may be searched to determine who is "on-duty." For example, if the central device is located in a surgical suite, it would not be useful to consider the schedules of staff members in an ICU. Thus, the search may be limited to the "surgical team" only.

In step 315, the method 300 detects a location associated with a first staff member who was registered at step 310. For example, the method 300 may detect an RFID tag of the first staff member via an RFID reader associated with the central device when the RFID tag is within a detection range of the RFID reader. In addition, a signal strength from a detectable RFID tag may further be used to approximate a distance from the RFID reader (or to approximate a distance from the central device).

In another example, step 315 may involve wireless detection of a mobile device of the first staff member. For instance, using a wireless transceiver, the method 300 may detect a MAC address or other identifier of the mobile device in wireless signals from the mobile device. Similarly, a signal strength of a wireless signal from the mobile device may be used to estimate a distance between the transceiver and the mobile device of the first staff member. Thus, the location of the first staff member can be detected or estimated if his or her RFID tag and/or mobile device are within detection range of an RFID reader or wireless transceiver of the central device. In still another example, a staff member may swipe a mobile device, RFID tag, or similar identification unit over a reader that uses near-field communications (NFC), such as Bluetooth low energy (BLE) or the like, when the staff member enters (or exits) the room of the central device to indicate the staff member's presence (or pending absence).

In step 320, the method 300 detects a location associated with a second staff member who was registered at step 310. Notably, step 320 may comprise the same or substantially similar operations to those of step 315, but with respect to a second staff member and his or her RFID tag and/or mobile device.

At step 325, the method 300 detects a first alarm from a first diagnostic device. For example, a wired connection may be deployed between the first diagnostic device and the central device, or the first diagnostic device may be configured to wirelessly send alarms to the central device via a wireless protocol, such as Bluetooth, BLE, ZigBee, Wi-Fi, or the like. The first diagnostic device may monitor one or more physiological parameters of a patient such as blood pressure, heart rate, breathing rate, temperature, oxygen level, and so forth, and may generate alarms under any of a number of detected conditions.

At step 330, the method 300 determines whether a second alarm is detected at the same time or at approximately the same time as the first alarm. For purposes of this determination at step 330, the first alarm and the second alarm may be simultaneous, or may be received sufficiently close in time, e.g., within the same second, within two seconds of one another, or within some other threshold duration of time, in order to trigger a prioritization between the two alarms. If a second alarm is detected, the method proceeds to step 335. Otherwise, the method 300 proceeds to step 340.

At step 335, the method 300 prioritizes the first alarm and the second alarm. In one example, a rule set is used to determine which of the first alarm and the second alarm should be presented first. For instance, a first diagnostic device may comprise a breathing monitor that detects that the patient is not breathing properly and issues a first alarm to the central device. However, a second diagnostic device may comprise a blood pressure monitor that detects that a patient's blood pressure has fallen below either or both threshold values of 90 mmHg systolic and 60 mmHg diastolic. This may trigger the second alarm which is sent to the central device. Given the simultaneous receipt of these two alarms, the method 300 may select to present the more critical alarm first, i.e., the first alarm relating to the breathing issue. It should be noted that in some situations, the first alarm and the second alarm may be generated by the same diagnostic device. For instance, some diagnostic devices are multi-tasked and may simultaneously be monitoring a number of different physiological parameters of a patient.

At step 340, the method 300 determines whether a manual override switch is activated. For instance, multiple staff members may register to receive remote notification messages at their mobile devices. However, a single staff member who is present in the same room as the one or more diagnostic devices and the centralized device may turn a switch "on" that indicates his or her presence in the room and which will suppress all notification messages which would otherwise be sent to remote staff members. For instance, a nurse may be changing the position of a heart rate monitor around a patient and does not want to trigger notification messages to remote staff members. During the repositioning, the heart rate monitor may fail to detect a pulse and generate an alarm. However, the attending nurse is aware that the patient is well, and that the alarm condition was caused by the repositioning procedure. Various other situations may warrant suppressing notification messages to remote staff members by using such a switch in this manner. In any case, when the nurse leaves the room or when circumstances otherwise warrant, the nurse may turn the switch "off," which will allow notification messages to again be sent to remote staff members in response to alarms from the one or more diagnostic devices. Accordingly, if at step 340 the method 300 determines that the switch is set or "on", the method proceeds to step 345. Otherwise, the method 300 proceeds to step 350.

At step 345, the method 300 presents a verbal alert, e.g., local to the central device using a speaker or other audio output unit. For example, the verbal alert may take the form of machine-generated speech such as "warning, blood pressure has fallen below ninety over sixty" or "warning, patient is not breathing properly." In one example, step 345 presents a first verbal alert relating to a first alarm that is prioritized over a second alarm. After, the first verbal alert is presented, a second verbal alert relating to the second alarm my then be presented. In one example, the second verbal alert is not presented until the first alarm is cleared. For instance, the second verbal alert may not be presented until the first verbal alert associated with the first alarm is acknowledged by at least one staff member, or the second verbal alert may simply not be presented until the first verbal alert has finished.

Alternatively, or in addition, step 345 may further include the first alarm and/or the second alarm being presented visually on a screen of the central device. For example, this may be useful as a supplement to verbal alerts where a staff member may fail to hear the entire verbal alert or may wish to clarify what was heard.

Following step 345, the method 300 proceeds to step 385 where the method determines whether to continue to monitor the one or more diagnostic devices. If it is determined to continue, the method 300 proceeds back to step 315. In particular, the method 300 may continue to return to step 315 so long as a patient is being monitored by the one or more diagnostic devices. Otherwise, the method 300 proceeds to step 395 where the method ends.

Returning to a discussion of step 340, if it is determined that a manual switch is not set, the method next proceeds to step 350.

At step 350, the method 300 determines whether the location associated with the first staff member is proximate to the central device. For instance, as described above, the location associated with the first staff member may be determined in accordance with step 315. In one example, the location associated with the first staff member is determined to be proximate to the central device when a signal strength from an RFID tag or mobile device of the first user is greater than a threshold signal strength. For instance, the threshold signal strength may be set by an operator to correspond to an approximate distance from the central device to a furthest point in a room in which the central device is situated. In another example, the threshold signal strength may be increased to also account for a staff member who may be located in an area just outside the room, but where verbal alerts from the central device may still be audible.

In still another example, a staff member may swipe a mobile device, RFID tag, or similar identification unit over a reader that uses near-field communications (NFC), such as Bluetooth low energy (BLE) or the like, to register the identification unit when the staff member enters the room of the central device. As such, the location associated with the first staff member may be determined to be proximate to the central device simply by virtue of the swiping of the identification unit across the near-field reader.

If at step 350 it is determined that the location associated with the first staff member is proximate to the central device, then the method 300 proceeds to step 355. At step 355, one or more verbal alerts may be presented via a local audio output unit of the central device. For example, step 355 may comprise the same or substantially similar operations to those discussed above in connection with step 340. However, if at step 350 it is determined that the location associated with the first staff member is not proximate to the central device, then the method 300 proceeds to step 360.

At step 360, the method 300 sends one or more notification messages to the first staff member who is determined to be remote from the central device. In one example, the method 300 uses a rule set that determines which one or more of a number of possible modes of communication should be used to send a notification message to a mobile device of the first staff member. For instance, a rule set may indicate that the first staff member should receive notification messages at his or her mobile device when not present, i.e., not proximate to the central device. The rule set may further specify that the notification messages should be sent via SMS or MMS message, via email, or using some other messaging format. Different rules may be set for different staff members. For example, some staff members may prefer to receive email notifications, while other staff members may prefer to receive text/SMS messages. In one example, a first notification message is sent with respect to a first alarm from a first diagnostic device that has been prioritized over a second alarm. After the first notification message is sent, a second notification may be sent with respect to the second alarm.

In one example, the second notification may not be sent until the first alarm is cleared. For example, the first alarm may be cleared when the first staff member acknowledges the receipt of the first notification message associated with the first alarm. For instance, the first staff member may send an acknowledgment message to the central device via the first staff member's mobile device. In another example, the first alarm is cleared upon an acknowledgement by any staff member who is present at the central device or who remotely receives a notification message based upon the first alarm. For instance, if another staff member acknowledges and assumes responsibility for attending to the first alarm, the first alarm may be "cleared" with respect to all staff members receiving notification messages from the central device. Alternatively, the first alarm may be cleared simply based upon the completion of the sending of the first notification message. The manner of "clearing" an alarm may vary depending upon the choices of the attending staff members, the nature of the particular condition triggering the alarm, and so forth.

In one example, the mobile device of the first staff member may include an application that is tasked with receiving notification messages and generating a local audio output, e.g., machine-generated speech via a speaker or other audio output component, based upon the notification message(s) that are received. In particular, some mobile devices may vibrate or beep whenever a text messages received, regardless of whether it is relating to an alarm from a diagnostic device or whether simply relating to personal matters. Thus, in one example, it is useful for the mobile device to automatically generate an audible output that reads the contents of the notification message.

Following step 360, the method 300 proceeds to step 365. In step 365, the method 300 determines if the location associated with the second staff member is proximate to the central device. In one example, step 360 comprises substantially similar operations to those described above in connection with step 350, only with respect to the second staff member.

If the location associated with the second staff member is determined to be proximate to the central device, then the method 300 proceeds to step 375. At step 375, the method 300 presents one or more verbal alerts locally, e.g., via an audio output unit of the central device. For instance, a first verbal alert based upon the first alarm may be presented, followed by a second verbal alert based upon the second alarm. Notably, step 375 may comprise the same or substantially similar operations to those described above in connection with steps 345 and 355. Following step 375, the method 300 proceeds to step 385.

Returning to a discussion of step 365, if at step 365 the location associated with the second staff member is not determined to be proximate to the central device, the method 300 proceeds to step 380. At step 380, the method 300 sends one or more remote notifications to a mobile device of the second staff member. In one example, step 380 comprises substantially similar operations to those described above in connection with step 360, only with respect to the second staff member.

Returning to a discussion of a different branch of the method 300, following step 355, the method 300 proceeds to step 370. In step 370, the method 300 determines if the location associated with the second staff member is proximate to the central device. In one example, step 370 is identical to step 365. If at step 370 it is determined that the location associated with the second staff member is not proximate to the central device, the method 300 proceeds to step 380 where the method continues as previously described. However, if at step 370 it is determined that the location associated with the second staff member is proximate to the central device, the method 300 simply proceeds to step 385. In particular, step 370 follows step 355 where the first and/or the second verbal alerts have already been presented via an audio output unit of the central device. Thus, it is not necessary to repeat such operations when it is determined that the location associated with the second staff member is also proximate to the central device.

As mentioned above, at step 385, the method 300 determines whether to continue. If the method 300 continues to monitor the one or more diagnostic devices, then the method proceeds back to step 315. Otherwise, the method 300 proceeds to step 395 where the method ends.

In addition, although not specifically specified, one or more steps, functions or operations of method 300 may include a storing, displaying and/or outputting step as required for a particular application. In other words, any data, records, fields, and/or intermediate results discussed in the method can be stored, displayed and/or outputted either on the device executing the method or to another device, as required for a particular application.

Furthermore, steps, blocks, functions or operations in FIG. 3 that recite a determining operation or involve a decision do not necessarily require that both branches of the determining operation be practiced. In other words, one of the branches of the determining operation can be deemed as an optional step. Moreover, steps, blocks, functions or operations of the above described method 300 can be combined, separated, and/or performed in a different order from that described above, without departing from the example embodiments of the present disclosure.

In this regard, it should also be noted that the method 300 is just one representative embodiment of the present disclosure and that several variations of the present method 300 may be derived in view of the disclosure herein. For example, for illustrative purposes, the method 300 considers only a first staff member and a second staff member. However, the method 300 may be readily expanded to address any number of staff members registered to receive remote notifications. In addition, although steps 345, 355 and 375 and indicated as separate steps in the method 300, in another example, a method may include a single step where it is determined to present a local verbal alert if any one or more staff members are proximate to the central device. Thus, these and other modifications are all contemplated within the scope of the present disclosure.

Figure 4:
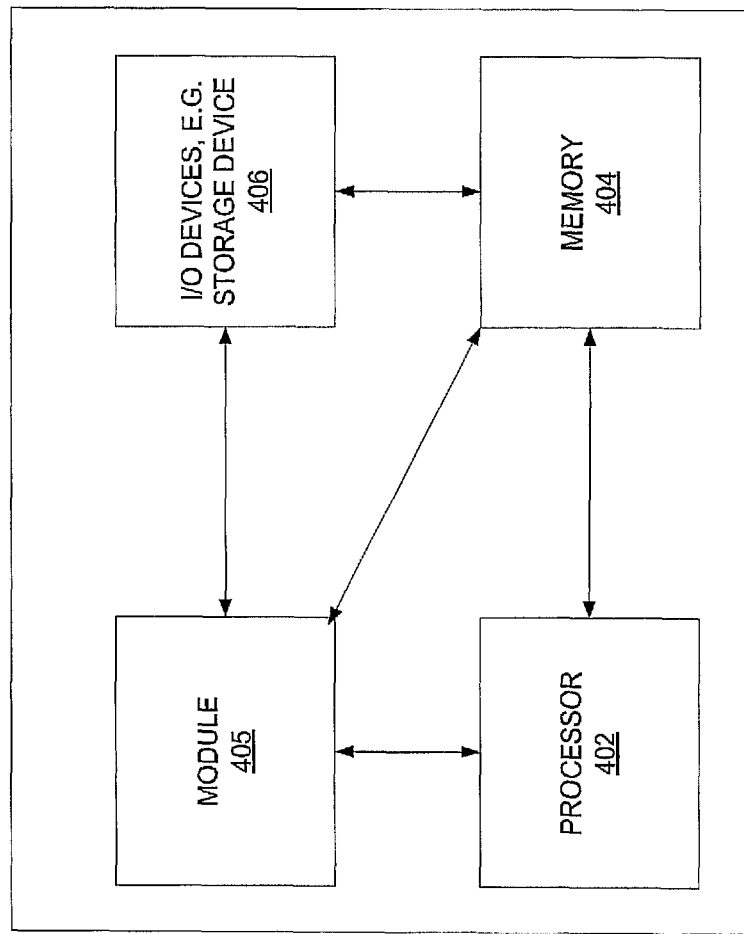
FIG. 4 illustrates a high-level block diagram of a computer suitable for use in performing the functions, methods and algorithms described herein.

FIG. 4 depicts a high-level block diagram of a computer suitable for use in performing the functions described herein. As depicted in FIG. 4, the system 400 comprises one or more hardware processor elements 402 (e.g., a central processing unit (CPU), a microprocessor, or a multi-core processor), a memory 404, e.g., random access memory (RAM) and/or read only memory (ROM), a module 405 for processing alarms, and various input/output devices 406 (e.g., storage devices, including but not limited to, a tape drive, a floppy drive, a hard disk drive or a compact disk drive, a receiver, a transmitter, a speaker or other audio output device, a display, a speech synthesizer, an output port, an input port and a user input device (such as a keyboard, a keypad, a mouse, a microphone and the like)). Although only one processor element is shown, it should be noted that the general-purpose computer may employ a plurality of processor elements. Furthermore, although only one general-purpose computer is shown in the Figure, if the method(s) as discussed above is implemented in a distributed or parallel manner for a particular illustrative example, i.e., the steps of the above method(s) or the entire method(s) are implemented across multiple or parallel computers, then the computer of this Figure is intended to represent each of those multiple computers. Furthermore, one or more hardware processors can be utilized in supporting a virtualized or shared computing environment. The virtualized computing environment may support one or more virtual machines representing computers, servers, or other computing devices. In such virtualized virtual machines, hardware components such as hardware processors and computer-readable storage devices may be virtualized or logically represented.

It should be noted that the present disclosure can be implemented in software and/or in a combination of software and hardware, e.g., using application specific integrated circuits (ASIC), a programmable logic array (PLA), including a field-programmable gate array (FPGA), or a state machine deployed on a hardware device, a general purpose computer or any other hardware equivalents, e.g., computer readable instructions pertaining to the method(s) discussed above can be used to configure a hardware processor to perform the steps, functions and/or operations of the above disclosed methods. In one embodiment, instructions and data for the present module or process 405 for processing alarms (e.g., a software program comprising computer-executable instructions) can be loaded into memory 404 and executed by hardware processor element 402 to implement the steps, functions or operations as discussed above in connection with the exemplary method 300. Furthermore, when a hardware processor executes instructions to perform "operations", this could include the hardware processor performing the operations directly and/or facilitating, directing, or cooperating with another hardware device or component (e.g., a co-processor and the like) to perform the operations.

The processor executing the computer readable or software instructions relating to the above described method(s) can be perceived as a programmed processor or a specialized processor. As such, the present module 505 for sterilizing a surface (including associated data structures) of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. Furthermore, a "tangible" computer-readable storage device or medium comprises a physical device, a hardware device, or a device that is discernible by the touch. More specifically, the computer-readable storage device may comprise any physical devices that provide the ability to store information such as data and/or instructions to be accessed by a processor or a computing device such as a computer or an application server.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A device, comprising:
a processor; and
a computer-readable medium storing instructions which, when executed by the processor, cause the processor to perform operations, the operations comprising:
receiving a first alarm from a first diagnostic device;
determining a location associated with a first user;
when the location associated with the first user is determined to be proximate to the device, presenting a first verbal alert indicating that the first diagnostic device is presenting the first alarm;
determining a location associated with a second user;
presenting the first verbal alert indicating that the first diagnostic device is presenting the first alarm, when the location associated with the second user is determined to be proximate to the device and when the first verbal alert has not previously been presented; and
when the location associated with the second user is determined to be not proximate to the device, sending a notification message to a mobile device of the second user indicating that the first diagnostic device is presenting the first alarm.

2. The device of claim 1, further comprising:
an audio output unit, for outputting the first verbal alert.

3. The device of claim 2, wherein the first verbal alert comprises a synthetic speech that is generated by the device based upon the first alarm.

4. The device of claim 1, wherein the mobile device comprises a second mobile device, wherein the device further comprises:
a wireless transceiver, wherein the determining the location associated with the first user comprises detecting a first mobile device of the first user via the wireless transceiver.

5. The device of claim 4, wherein the determining the location associated with the first user comprises:
determining that the location associated with the first user is proximate to the first diagnostic device when a strength of a wireless signal from the first mobile device exceeds a predefined threshold signal strength.

6. The device of claim 1, further comprising:
a radio frequency identification reader, wherein the determining the location associated with the first user comprises detecting a radio frequency identification tag of the first user via the radio frequency identification reader.

7. The device of claim 1, wherein the operations further comprise:
receiving a second alarm;
determining that the first alarm has a priority over the second alarm;
clearing the first alarm; and
when the location associated with the first user is determined to be proximate to the device and after the first alarm is cleared, presenting an additional verbal alert that is based upon the second alarm.

8. The device of claim 7, wherein the first alarm is cleared upon a completion of the first verbal alert.

9. The device of claim 7, wherein the first alarm is cleared upon an acknowledgement of the first alarm.

10. The device of claim 7, wherein the mobile device comprises a second mobile device, wherein the notification message comprises a second notification message, wherein the first alarm is cleared upon the sending of a first notification message to a first mobile device of the first user.

11. The device of claim 10, wherein the first notification message comprises at least one of: an email message, a short message service message, and a multimedia message service message.

12. The device of claim 10, wherein the first notification message causes the first verbal alert to be presented via an audio output component of the first mobile device.

13. The device of claim 10, where the operations further comprise:
registering the first mobile device of the first user to receive notification messages.

14. The device of claim 13, wherein the registering the first mobile device of the first user comprises:
retrieving scheduling information, wherein the scheduling information includes information on a schedule of the first user;
determining that the first user is on-duty; and
registering the first mobile device of the first user to receive the notification messages when it is determined that the first user is on-duty.

15. The device of claim 10, further comprising:
an override switch, wherein when the override switch is activated, the sending of the first notification message is disabled, and when the override switch is deactivated, the sending of the first notification message is enabled.

16. The device of claim 15, wherein the override switch is activated and deactivated by the first user.

17. The device of claim 1, further comprising:
a screen for displaying information from the first alarm.

18. A non-transitory computer-readable medium storing instructions which, when executed by a processor, cause the processor to perform operations, the operations comprising:
receiving a first alarm from a first diagnostic device;
determining a location associated with a first user;
when the location associated with the first user is determined to be proximate to a device, presenting a first verbal alert indicating that the first diagnostic device is presenting the first alarm;
determining a location associated with a second user;
presenting the first verbal alert indicating that the first diagnostic device is presenting the first alarm, when the location associated with the second user is determined to be proximate to the device and when the first verbal alert has not previously been presented; and
when the location associated with the second user is determined to be not proximate to the device, sending a notification message to a mobile device of the second user indicating that the first diagnostic device is presenting the first alarm.

19. A method, comprising:
receiving, by a processor, a first alarm from a first diagnostic device;
determining, by the processor, a location associated with a first user;
when the location associated with the first user is determined to be proximate to a device, presenting, by the processor, a first verbal alert indicating that the first diagnostic device is presenting the first alarm;
determining a location associated with a second user;
presenting the first verbal alert indicating that the first diagnostic device is presenting the first alarm, when the location associated with the second user is determined to be proximate to the device and when the first verbal alert has not previously been presented; and
when the location associated with the second user is determined to be not proximate to the device, sending a notification message to a mobile device of the second user indicating that the first diagnostic device is presenting the first alarm.

* * * * *